(12) United States Patent
Hu et al.

(10) Patent No.: US 9,440,357 B2
(45) Date of Patent: Sep. 13, 2016

(54) SYSTEM FOR STABILIZATION CONTROL OF MOBILE ROBOTICS

(76) Inventors: John Hu, Boxborough, MA (US); Yi-Je Lim, Boxborough, MA (US)

( * ) Notice: Subject to any disclaimer, the term of this patent is extended or adjusted under 35 U.S.C. 154(b) by 68 days.

(21) Appl. No.: 13/461,728

(22) Filed: May 1, 2012

(65) Prior Publication Data

US 2012/0283872 A1 Nov. 8, 2012

Related U.S. Application Data

(60) Provisional application No. 61/518,096, filed on May 2, 2011.

(51) Int. Cl.
| | | |
|---|---|---|
| G06F 19/00 | (2011.01) | |
| B25J 11/00 | (2006.01) | |
| B25J 5/00 | (2006.01) | |

(52) U.S. Cl.
CPC .............. B25J 11/009 (2013.01); B25J 5/007 (2013.01)

(58) Field of Classification Search
CPC ...... B62D 57/028; B25J 5/007; B25J 11/009
See application file for complete search history.

(56) References Cited

U.S. PATENT DOCUMENTS

| | | | | |
|---|---|---|---|---|
| 3,015,497 A * | 1/1962 | Aldred, Jr. | ............... | 280/755 |
| 7,057,367 B2 * | 6/2006 | Furuta et al. | ............. | 318/568.12 |
| 7,114,747 B2 * | 10/2006 | Dix et al. | ................... | 280/764.1 |
| 7,719,222 B2 * | 5/2010 | Theobald | ................. | 318/568.12 |
| 7,902,784 B1 * | 3/2011 | Theobald | ................. | 318/568.1 |
| 8,082,811 B2 * | 12/2011 | Udono | ......................... | 73/865.9 |
| 8,102,134 B1 * | 1/2012 | Theobald | ................. | 318/568.21 |
| 8,106,616 B1 * | 1/2012 | Theobald | ................. | 318/568.2 |
| 8,386,076 B2 * | 2/2013 | Honda et al. | ................ | 700/245 |
| 8,793,015 B2 * | 7/2014 | Hasegawa et al. | ........... | 700/245 |
| 2005/0209614 A1 * | 9/2005 | Fenter et al. | .................. | 606/153 |
| 2006/0097683 A1 * | 5/2006 | Hosoda et al. | ........... | 318/568.12 |
| 2007/0152427 A1 * | 7/2007 | Olsen | ............................ | 280/649 |
| 2008/0265821 A1 * | 10/2008 | Theobald | ................. | 318/568.12 |
| 2009/0114460 A1 * | 5/2009 | Amino et al. | .................. | 180/8.3 |
| 2012/0328395 A1 * | 12/2012 | Jacobsen et al. | ................. | 414/1 |

FOREIGN PATENT DOCUMENTS

JP 2006053731 A * 2/2006

OTHER PUBLICATIONS

Yanjie Li, Dynamic Stability Analyses Based on ZMP of a Wheel-based Humanoid Robot, 2006, IEEE International Conference on Robotics and Biomimetics, p. 1565-1570.*
Aarne Halme, Robot motion by simultaneously wheel and leg propulsion, 2001, Automation Technology Laboratory Helsinki University of Technology.*
Ilkka Leppanen, Sensing Terrain Parameters and the Characteristice of Vehicle-terrain Interaction Using the Locomotion System of a Robot, 2010, In-Tech.*

* cited by examiner

*Primary Examiner* — Khoi Tran
*Assistant Examiner* — Ryan Rink
(74) *Attorney, Agent, or Firm* — Ariel S. Bentolila; Bay Area IP Group LLC (57) ABSTRACT

A system comprises a platform being configured for locomotion in a plurality of directions over a surface. A robotic unit is configured for dexterous manipulation comprising at least lifting of objects. The robotic unit is joined to the platform. At least one extender unit is joined to the platform and is configured for controlled extension beyond the platform to contact the surface to stabilize the system at least during the manipulation by the robotic unit. At least one controlling unit is configured to be operable for at least determining a center of gravity and a zero moment point for the system and for at least controlling an extension of the extender unit.

14 Claims, 9 Drawing Sheets

$$x_{ZMP} = \frac{\sum_{i=1}^{N}\{\vec{r}_i \times m_i(\vec{a}_i - \vec{g}) + [d(\vec{I}_i \vec{\omega}_i)/dt]\}_y}{M(\ddot{Z}_{CM} + g)}$$

FIG. 5a $$y_{ZMP} = \frac{\sum_{i=1}^{N}\{\vec{r}_i \times m_i(\vec{a}_i - \vec{g}) + [d(\vec{I}_i \vec{\omega}_i)/dt]\}_x}{M(\ddot{Z}_{CM} + g)}$$

FIG. 5b $$x_{ZMP} = x_{CM} - \frac{F_x}{F_z + Mg}z_{CM} - \frac{\tau_y(\vec{F}_{CM})}{F_z + Mg}$$

FIG. 5c $$y_{ZMP} = y_{CM} - \frac{F_y}{F_z + Mg}z_{CM} - \frac{\tau_x(\vec{F}_{CM})}{F_z + Mg}$$

SYSTEM FOR STABILIZATION CONTROL OF MOBILE ROBOTICS

CROSS-REFERENCE TO RELATED APPLICATIONS

The present Utility patent application claims priority benefit of the U.S. provisional application for patent Ser. No. 61/518,096 filed on May 2, 2011 under 35 U.S.C. 119(e). The contents of this related provisional application are incorporated herein by reference for all purposes to the extent that such subject matter is not inconsistent herewith or limiting hereof.

FEDERALLY SPONSORED RESEARCH OR DEVELOPMENT

This patent is partially developed through US Army SBIR Phase 2 Project under Contract W81XWH-08-C-0002 with project title: An Advanced Medical Robotic System Augmenting Healthcare Capabilities, and US Army STTR Phase 2 Project under Contract W81XWH-08-C-0116 entitled as Robotic Neck and Spinal Injury Assessment Device.

REFERENCE TO SEQUENCE LISTING, A TABLE, OR A COMPUTER LISTING APPENDIX

Not applicable.

COPYRIGHT NOTICE

A portion of the disclosure of this patent document contains material that is subject to copyright protection. The copyright owner has no objection to the facsimile reproduction by anyone of the patent document or patent disclosure as it appears in the Patent and Trademark Office, patent file or records, but otherwise reserves all copyright rights whatsoever.

FIELD OF THE INVENTION

One or more embodiments of the invention generally relate to zero moment point (ZMP) stability. More particularly, one or more embodiments of the invention relate to a mobility stabilization system for robots.

BACKGROUND OF THE INVENTION

The following background information may present examples of specific aspects of the prior art (e.g., without limitation, approaches, facts, or common wisdom) that, while expected to be helpful to further educate the reader as to additional aspects of the prior art, is not to be construed as limiting the present invention, or any embodiments thereof, to anything stated or implied therein or inferred thereupon.

The following is an example of a specific aspect in the prior art that, while expected to be helpful to further educate the reader as to additional aspects of the prior art, is not to be construed as limiting the present invention, or any embodiments thereof, to anything stated or implied therein or inferred thereupon. By way of educational background, another aspect of the prior art generally useful to be aware of is that a robot is a mechanical or virtual intelligent agent that can perform tasks automatically or with guidance, typically by remote control. In practice a robot is usually an electro-mechanical machine that is guided by computer and electronic programming. By mimicking a lifelike appearance or automating movements, a robot may convey a sense that it has intent or agency of its own.

Typically, ZMP is a concept related with dynamics and control of legged locomotion, e.g., for humanoid robots. It specifies the point with respect to which dynamic reaction force at the contact of the foot with the ground does not produce any moment in the horizontal direction, i.e. the point where total of vertical inertia and gravity forces equals zero.

In view of the foregoing, it is clear that these traditional techniques are not perfect and leave room for more optimal approaches.

BRIEF DESCRIPTION OF THE DRAWINGS

The present invention is illustrated by way of example, and not by way of limitation, in the figures of the accompanying drawings and in which like reference numerals refer to similar elements and in which:

FIGS. 1a, 1b, and 1c illustrate an exemplary mobile robot stability system, in accordance with an embodiment of the present invention, where FIG. 1a illustrates the platform with the wheeled extender portion retracted, FIG. 1b illustrates the platform with the motorized supporting bar extended, and FIG. 1c illustrates the platform with the legged extender extended, in accordance with an embodiment of the present invention;

FIGS. 2a and 2b illustrate an exemplary mobile robot stability system with the robot joined to the mobile platform, in accordance with an embodiment of the present invention, where FIG. 2a illustrates the robot lowering the body posture to engage a human in an exemplary position, and FIG. 2b illustrates the robot lifting the human in an upright body posture in an exemplary position, in accordance with an embodiment of the present invention;

FIGS. 6a and 6b illustrate a detailed perspective view of an exemplary mobile robot stability system with an extended stability zone on the side, in accordance with an embodiment of the present invention, where FIG. 6a shows a robot maneuvering to the side in a small area, and FIG. 6b shows the platform with a ZMP stable region on the side, corresponding to the extension of the side extension portion, in accordance with an embodiment of the present invention.

Unless otherwise indicated illustrations in the figures are not necessarily drawn to scale.

DETAILED DESCRIPTION OF SOME EMBODIMENTS

Embodiments of the present invention are best understood by reference to the detailed figures and description set forth herein.

Embodiments of the invention are discussed below with reference to the Figures. However, those skilled in the art will readily appreciate that the detailed description given herein with respect to these figures is for explanatory purposes as the invention extends beyond these limited embodiments. For example, it should be appreciated that those skilled in the art will, in light of the teachings of the present invention, recognize a multiplicity of alternate and suitable approaches, depending upon the needs of the particular application, to implement the functionality of any given detail described herein, beyond the particular implementation choices in the following embodiments described and shown. That is, there are numerous modifications and variations of the invention that are too numerous to be listed but that all fit within the scope of the invention. Also, singular words should be read as plural and vice versa and masculine as feminine and vice versa, where appropriate, and alternative embodiments do not necessarily imply that the two are mutually exclusive.

It is to be further understood that the present invention is not limited to the particular methodology, compounds, materials, manufacturing techniques, uses, and applications, described herein, as these may vary. It is also to be understood that the terminology used herein is used for the purpose of describing particular embodiments only, and is not intended to limit the scope of the present invention. It must be noted that as used herein and in the appended claims, the singular forms "a," "an," and "the" include the plural reference unless the context clearly dictates otherwise. Thus, for example, a reference to "an element" is a reference to one or more elements and includes equivalents thereof known to those skilled in the art. Similarly, for another example, a reference to "a step" or "a means" is a reference to one or more steps or means and may include sub-steps and subservient means. All conjunctions used are to be understood in the most inclusive sense possible. Thus, the word "or" should be understood as having the definition of a logical "or" rather than that of a logical "exclusive or" unless the context clearly necessitates otherwise. Structures described herein are to be understood also to refer to functional equivalents of such structures. Language that may be construed to express approximation should be so understood unless the context clearly dictates otherwise.

Unless defined otherwise, all technical and scientific terms used herein have the same meanings as commonly understood by one of ordinary skill in the art to which this invention belongs. Preferred methods, techniques, devices, and materials are described, although any methods, techniques, devices, or materials similar or equivalent to those described herein may be used in the practice or testing of the present invention. Structures described herein are to be understood also to refer to functional equivalents of such structures. The present invention will now be described in detail with reference to embodiments thereof as illustrated in the accompanying drawings.

From reading the present disclosure, other variations and modifications will be apparent to persons skilled in the art. Such variations and modifications may involve equivalent and other features which are already known in the art, and which may be used instead of or in addition to features already described herein.

Although Claims have been formulated in this Application to particular combinations of features, it should be understood that the scope of the disclosure of the present invention also includes any novel feature or any novel combination of features disclosed herein either explicitly or implicitly or any generalization thereof, whether or not it relates to the same invention as presently claimed in any Claim and whether or not it mitigates any or all of the same technical problems as does the present invention.

Features which are described in the context of separate embodiments may also be provided in combination in a single embodiment. Conversely, various features which are, for brevity, described in the context of a single embodiment, may also be provided separately or in any suitable subcombination. The Applicants hereby give notice that new Claims may be formulated to such features and/or combinations of such features during the prosecution of the present Application or of any further Application derived therefrom.

References to "one embodiment," "an embodiment," "example embodiment," "various embodiments," etc., may indicate that the embodiment(s) of the invention so described may include a particular feature, structure, or characteristic, but not every embodiment necessarily includes the particular feature, structure, or characteristic. Further, repeated use of the phrase "in one embodiment," or "in an exemplary embodiment," do not necessarily refer to the same embodiment, although they may.

As is well known to those skilled in the art many careful considerations and compromises typically must be made when designing for the optimal manufacture of a commercial implementation any system, and in particular, the embodiments of the present invention. A commercial implementation in accordance with the spirit and teachings of the present invention may configured according to the needs of the particular application, whereby any aspect(s), feature(s), function(s), result(s), component(s), approach(es), or step(s) of the teachings related to any described embodiment of the present invention may be suitably omitted, included, adapted, mixed and matched, or improved and/or optimized by those skilled in the art, using their average skills and known techniques, to achieve the desired implementation that addresses the needs of the particular application.

In the following description and claims, the terms "coupled" and "connected," along with their derivatives, may be used. It should be understood that these terms are not intended as synonyms for each other. Rather, in particular embodiments, "connected" may be used to indicate that two or more elements are in direct physical or electrical contact with each other. "Coupled" may mean that two or more elements are in direct physical or electrical contact. However, "coupled" may also mean that two or more elements are not in direct contact with each other, but yet still cooperate or interact with each other.

A "computer" may refer to one or more apparatus and/or one or more systems that are capable of accepting a structured input, processing the structured input according to prescribed rules, and producing results of the processing as output. Examples of a computer may include: a computer; a stationary and/or portable computer; a computer having a single processor, multiple processors, or multi-core processors, which may operate in parallel and/or not in parallel; a general purpose computer; a supercomputer; a mainframe; a super mini-computer; a mini-computer; a workstation; a micro-computer; a server; a client; an interactive television; a web appliance; a telecommunications device with internet access; a hybrid combination of a computer and an interactive television; a portable computer; a tablet personal computer (PC); a personal digital assistant (PDA); a portable telephone; application-specific hardware to emulate a computer and/or software, such as, for example, a digital signal processor (DSP), a field-programmable gate array (FPGA), an application specific integrated circuit (ASIC), an application specific instruction-set processor (ASIP), a chip, chips, a system on a chip, or a chip set; a data acquisition device; an optical computer; a quantum computer; a biological computer; and generally, an apparatus that may accept data, process data according to one or more stored software programs, generate results, and typically include input, output, storage, arithmetic, logic, and control units.

"Software" may refer to prescribed rules to operate a computer. Examples of software may include: code segments in one or more computer-readable languages; graphical and or/textual instructions; applets; pre-compiled code; interpreted code; compiled code; and computer programs.

A "computer-readable medium" may refer to any storage device used for storing data accessible by a computer. Examples of a computer-readable medium may include: a magnetic hard disk; a floppy disk; an optical disk, such as a CD-ROM and a DVD; a magnetic tape; a flash memory; a memory chip; and/or other types of media that can store machine-readable instructions thereon.

A "computer system" may refer to a system having one or more computers, where each computer may include a computer-readable medium embodying software to operate the computer or one or more of its components. Examples of a computer system may include: a distributed computer system for processing information via computer systems linked by a network; two or more computer systems connected together via a network for transmitting and/or receiving information between the computer systems; a computer system including two or more processors within a single computer; and one or more apparatuses and/or one or more systems that may accept data, may process data in accordance with one or more stored software programs, may generate results, and typically may include input, output, storage, arithmetic, logic, and control units.

A "network" may refer to a number of computers and associated devices that may be connected by communication facilities. A network may involve permanent connections such as cables or temporary connections such as those made through telephone or other communication links. A network may further include hard-wired connections (e.g., coaxial cable, twisted pair, optical fiber, waveguides, etc.) and/or wireless connections (e.g., radio frequency waveforms, free-space optical waveforms, acoustic waveforms, etc.). Examples of a network may include: an internet, such as the Internet; an intranet; a local area network (LAN); a wide area network (WAN); and a combination of networks, such as an internet and an intranet.

Exemplary networks may operate with any of a number of protocols, such as Internet protocol (IP), asynchronous transfer mode (ATM), and/or synchronous optical network (SONET), user datagram protocol (UDP), IEEE 802.x, etc.

Embodiments of the present invention may include apparatuses for performing the operations disclosed herein. An apparatus may be specially constructed for the desired purposes, or it may comprise a general-purpose device selectively activated or reconfigured by a program stored in the device.

Embodiments of the invention may also be implemented in one or a combination of hardware, firmware, and software. They may be implemented as instructions stored on a machine-readable medium, which may be read and executed by a computing platform to perform the operations described herein.

In the following description and claims, the terms "computer program medium" and "computer readable medium" may be used to generally refer to media such as, but not limited to, removable storage drives, a hard disk installed in hard disk drive, and the like. These computer program products may provide software to a computer system. Embodiments of the invention may be directed to such computer program products.

An algorithm is here, and generally, considered to be a self-consistent sequence of acts or operations leading to a desired result. These include physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers or the like. It should be understood, however, that all of these and similar terms are to be associated with the appropriate physical quantities and are merely convenient labels applied to these quantities.

Unless specifically stated otherwise, and as may be apparent from the following description and claims, it should be appreciated that throughout the specification descriptions utilizing terms such as "processing," "computing," "calculating," "determining," or the like, refer to the action and/or processes of a computer or computing system, or similar electronic computing device, that manipulate and/or transform data represented as physical, such as electronic, quantities within the computing system's registers and/or memories into other data similarly represented as physical quantities within the computing system's memories, registers or other such information storage, transmission or display devices.

In a similar manner, the term "processor" may refer to any device or portion of a device that processes electronic data from registers and/or memory to transform that electronic data into other electronic data that may be stored in registers and/or memory. A "computing platform" may comprise one or more processors.

A non-transitory computer readable medium includes, but is not limited to, a hard drive, compact disc, flash memory, volatile memory, random access memory, magnetic memory, optical memory, semiconductor based memory, phase change memory, optical memory, periodically refreshed memory, and the like; however, the non-transitory computer readable medium does not include a pure transitory signal per se; i.e., where the medium itself is transitory.

It is to be understood that any exact measurements/ dimensions or particular construction materials indicated herein are solely provided as examples of suitable configurations and are not intended to be limiting in any way. Depending on the needs of the particular application, those skilled in the art will readily recognize, in light of the following teachings, a multiplicity of suitable alternative implementation details.

FIGS. 1 through 7 illustrate some exemplary embodiments and various views of a mobile robot stability system 100 and ZMP stability concepts applied to a mobile robot 102, in accordance with at least some embodiments of the present invention. Some embodiments of the present invention may include the mobile robot stability system 100 that provides stability for the robot 102, especially during dexterous manipulation, including, without limitation, lifting heavy objects, rescuing wounded soldiers in battlefield, maneuvering by means of, but not limited to, wheels, holonomic drive, or tracks through rough terrain, and performing duties while moving. The mobile robot stability system 100 may provide complete static (center of gravity) and dynamic (zero moment point) stability capabilities for the robot, and may operate independently numerous other functions the robot may perform. The mobile robot stability system 100 may include a platform 104 that utilizes a mounting portion 106 for the robot 102 to join with. The platform may utilize a various drive system for mobility in a multiplicity of directions. A ZMP extender 108 may extend from the platform to support the robot, to prevent the robot from tipping over, and to maintain dynamic stability during a manipulation process. While extended, the area covered by the ZMP extender may create a ZMP stable area 110, which may comprise a polygon area within the robot foothold. The robot may move with dynamic stability by remaining its center of gravity within the ZMP stable area. The body posture of the robot may also be dynamically controlled to enhance stability. The mobile robot stability system 100 performs a real-time ZMP computation method for dynamically estimating the stability of the platform during movement. The ZMP computation method eliminates the need for counter weights to be attached to the robot.

Figure 1A:
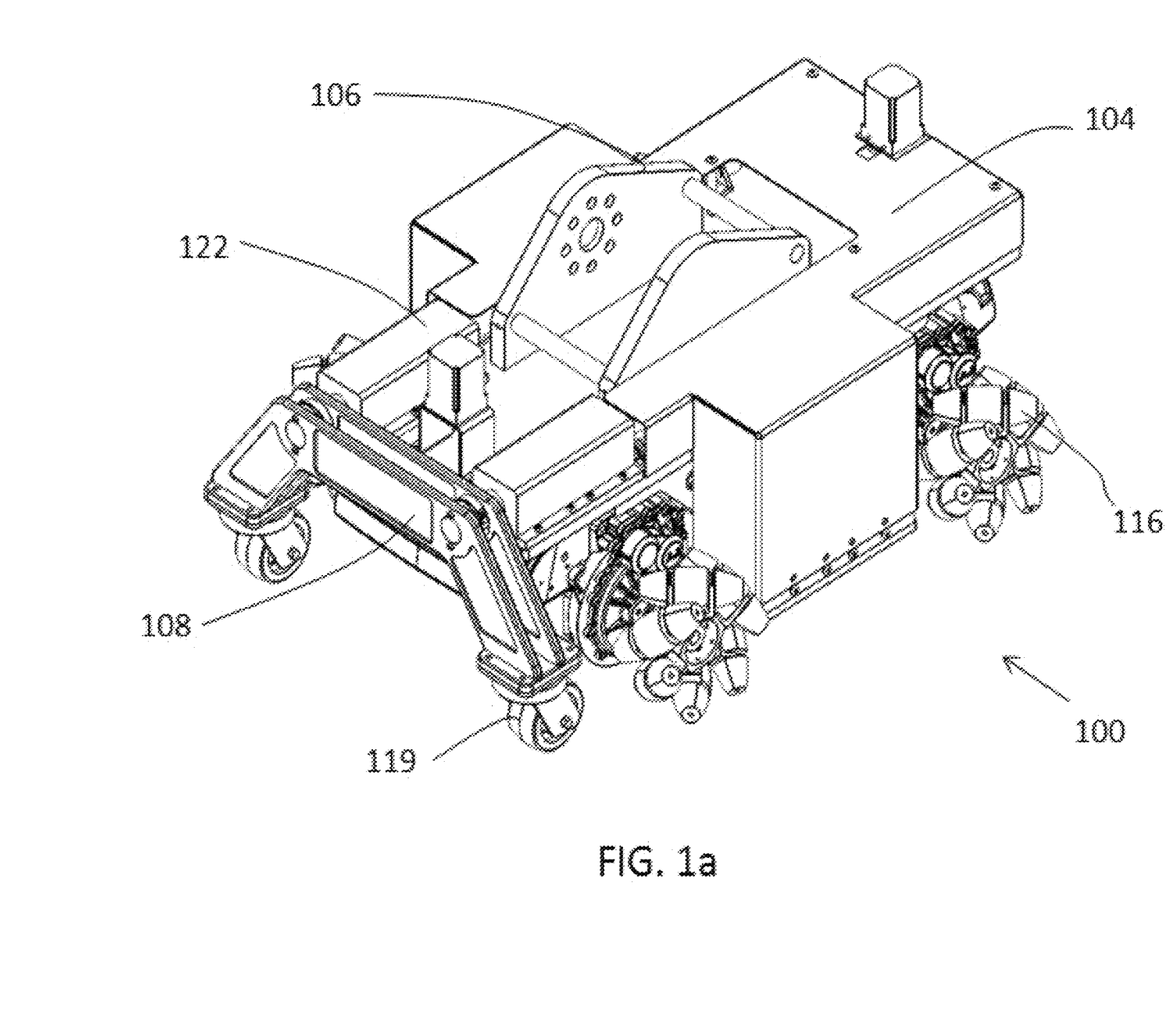
Figure 1B:
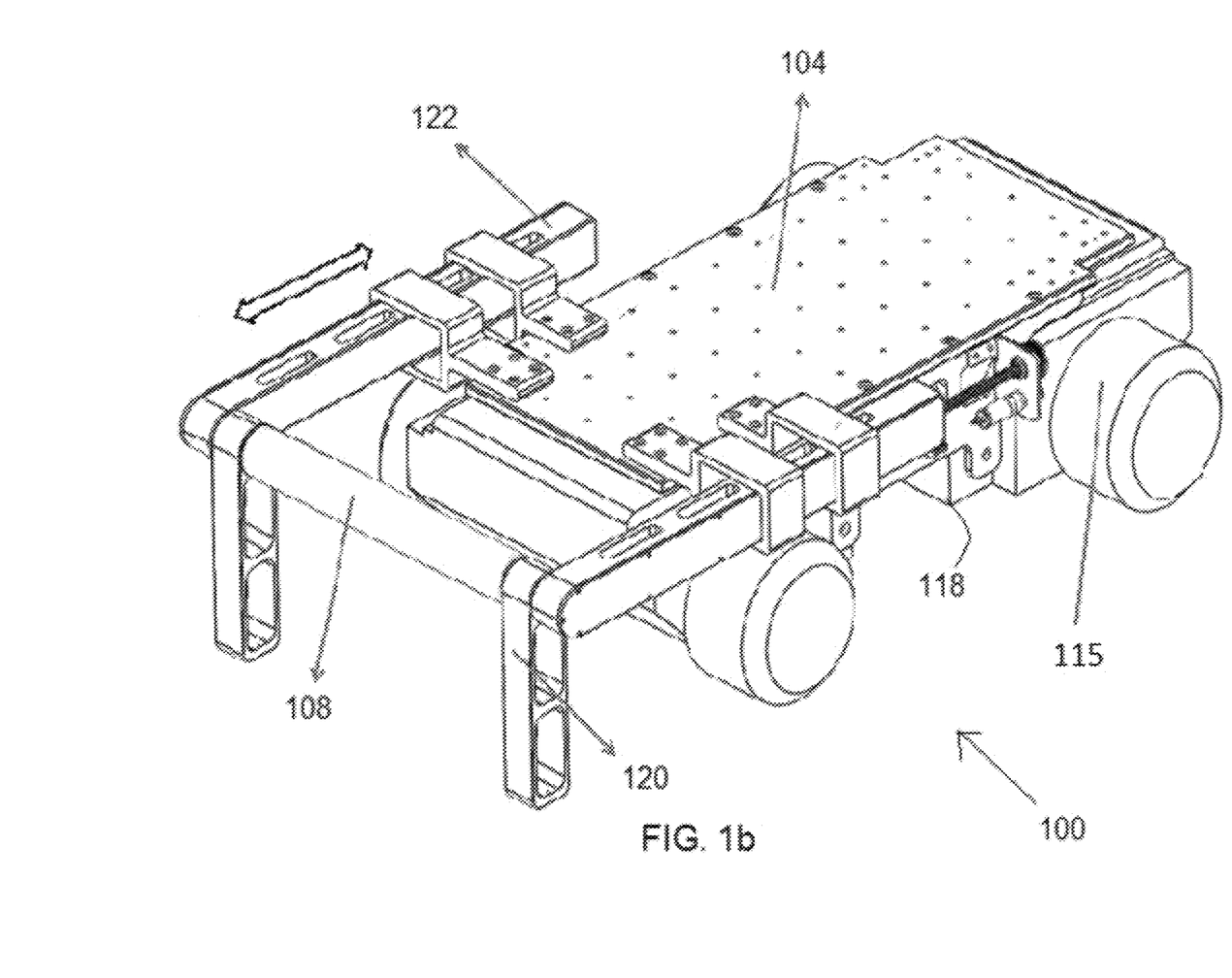
Figure 1C:
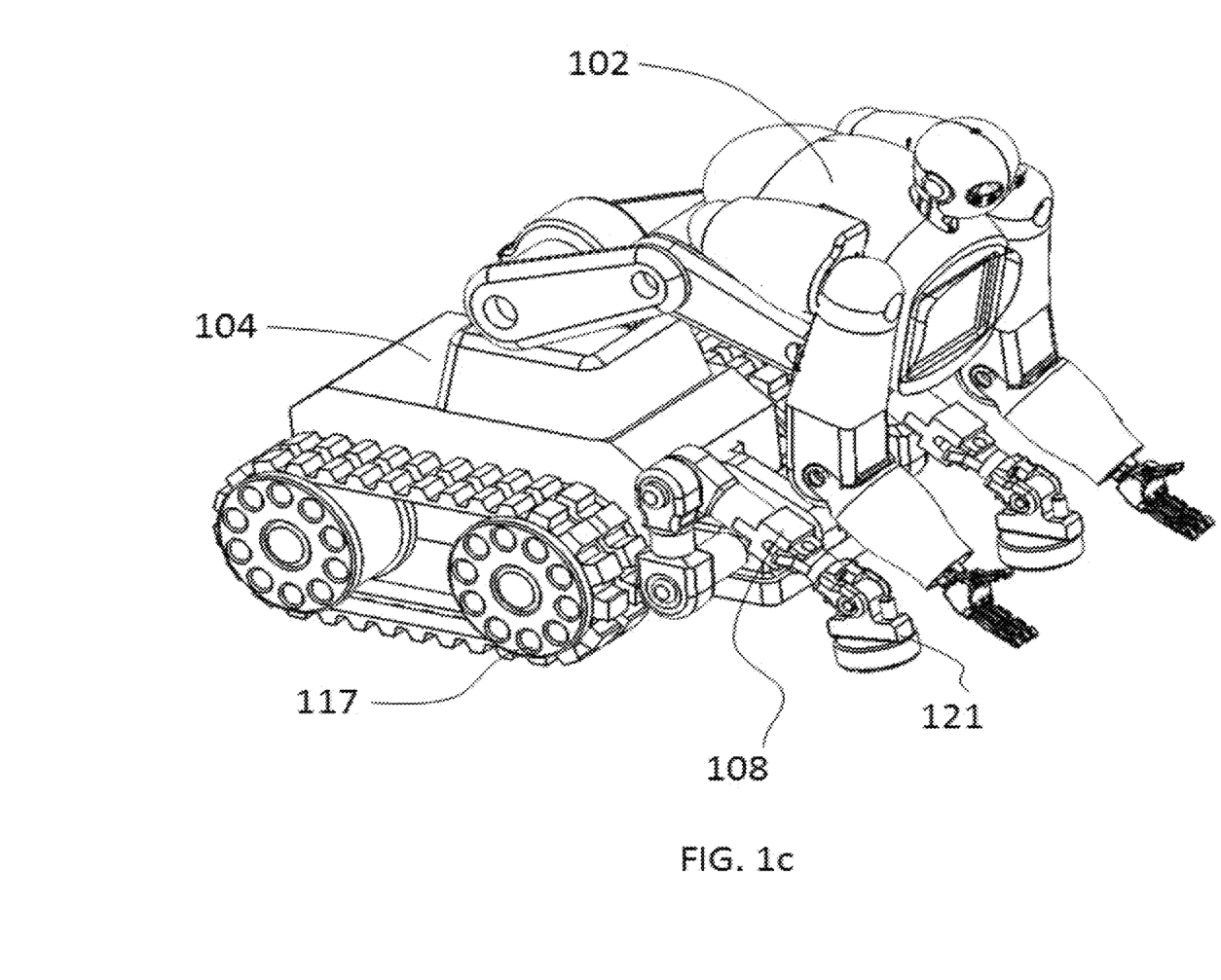

FIGS. 1a, 1b, and 1c illustrate an exemplary mobile robot stability system 100, in accordance with an embodiment of the present invention, where FIG. 1a illustrates the mobile platform with the wheeled extender portion retracted, FIG. 1b illustrates the mobile platform with the motorized supporting bar extended, and FIG. 1c illustrates the mobile platform with the legged extender extended, in accordance with at least some embodiments of the present invention. In some embodiments, the platform may provide a foundation for the mobile robot stability system. The ZMP extender may include, without limitation, wheeled supporters 119, motorized supporting bars 120, or articulated legs 121 to support the vertical load. The platform may move through multiple means, including, without limitation, regular wheels 115, holonomic drive 116, and tracks 117. The mobile platform 104 may permit the variety of directions to carry the robot and other components in tight spaces, and avoid obstacles. Those skilled in the art, in light of the present teachings will recognize that multi-directional movement may be coordinated with body posture control to further enhance stability. The posture control may require nominal adjustments during normal uses. When the robot performs tasks like weight lifting, the mobile robot stability system may extend out at least one supporting leg for expanding a ZMP stable region 110. The platform 104 and robot 102 may maintain dynamic stability as long as the dynamic center of mass (CM) of the mobile system stays within the ZMP stabile region.

In some embodiments, the platform 104 may include a mounting portion 106 to join a robot, including, without limitation, a robot upper torso, a humanoid robot, and a crane-like mechanism to the platform. In some embodiments, the robot 102 may join with the mounting portion 106 with fasteners, including, without limitation bolts, screws, welding, adhesives, and the like. A motor actuator 118 may provide power to activate the ZMP stabilizer and other components joined to the platform. In some embodiments, the articulated legs 121 may provide legged locomotion for the platform.

In some embodiments, at least one side bar 122 may slide along the side portions of the platform 104 to mechanically extend and retract the extender portion. In some embodiments, at least one support leg 121 may extend substantially from the extender portion to provide legged locomotion for the platform. Those skilled in the art, in light of the present invention, will recognize that both at least one support leg and at least one side bar may work in conjunction to propel the mobile robot stability system. In some embodiments, a side extension portion 114 engages the ground surface to provide additional stability in small areas. Those skilled in the art, in light of the present teachings will recognize that the side extension portion, when extended, creates an additional ZMP stable region 110 to the side, similar to the ZMP stable region 110 created by the extender portion. The ZMP stable region 110 may enhance the stability of the mobile robot stability system, especially while lifting heavy weights. Suitable materials for fabrication of the platform include, without limitation, steel, titanium, plastic, rubber, silicone, and the like.

Figure 2A:
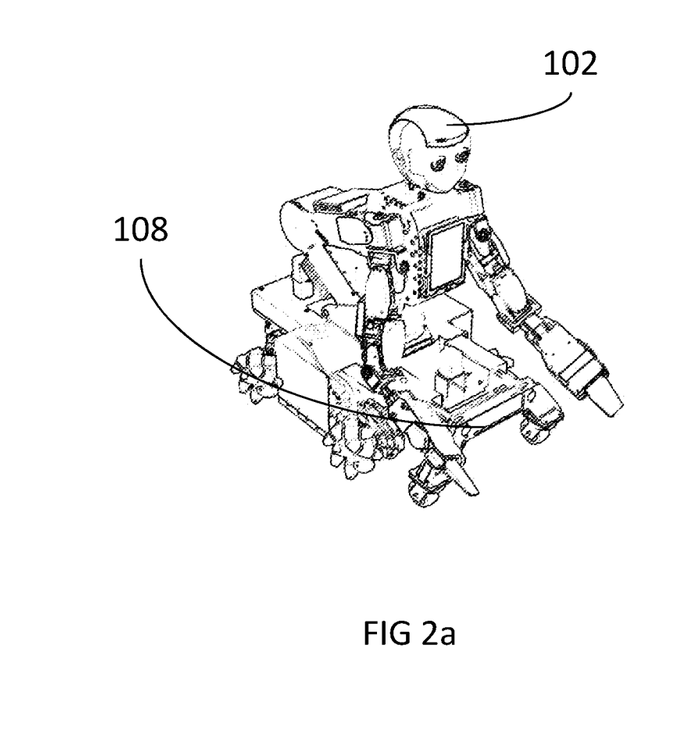
Figure 2B:
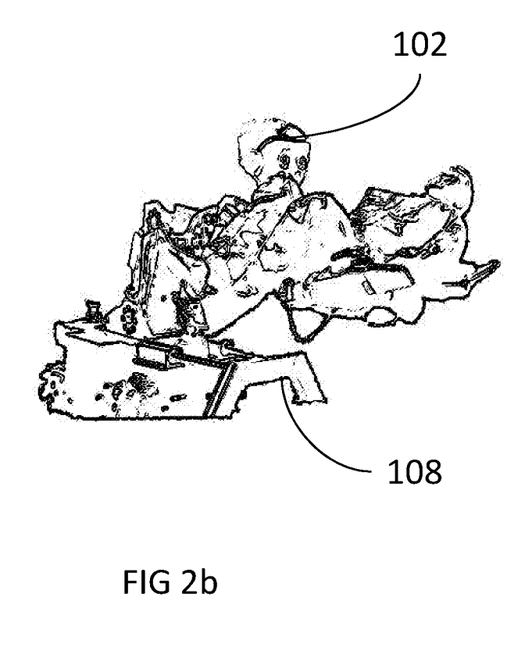

FIGS. 2a and 2b illustrate an exemplary mobile robot stability system with the robot joined to the mobile platform, in accordance with an embodiment of the present invention, where FIG. 2a illustrates the robot 102 lowering the body posture to engage a human in an exemplary position, and FIG. 2b illustrates the robot 102 lifting the human in an upright body posture in an exemplary position, in accordance with at least some embodiments of the present invention. In some embodiments, the extender portion 108 may remain retracted prior to lifting the human. After engaging the human, the extender portion 108 may extend to provide a ZMP stable region. The point of contact between at least one wheel and the ground surface may include a horizontal component of the moment of ground reaction force is substantially zero at the point where total of vertical inertia and gravity forces equals zero. Those skilled in the art, in light of the present teachings will recognize that the zero horizontal components create minimal movement and sliding.

Figure 3:
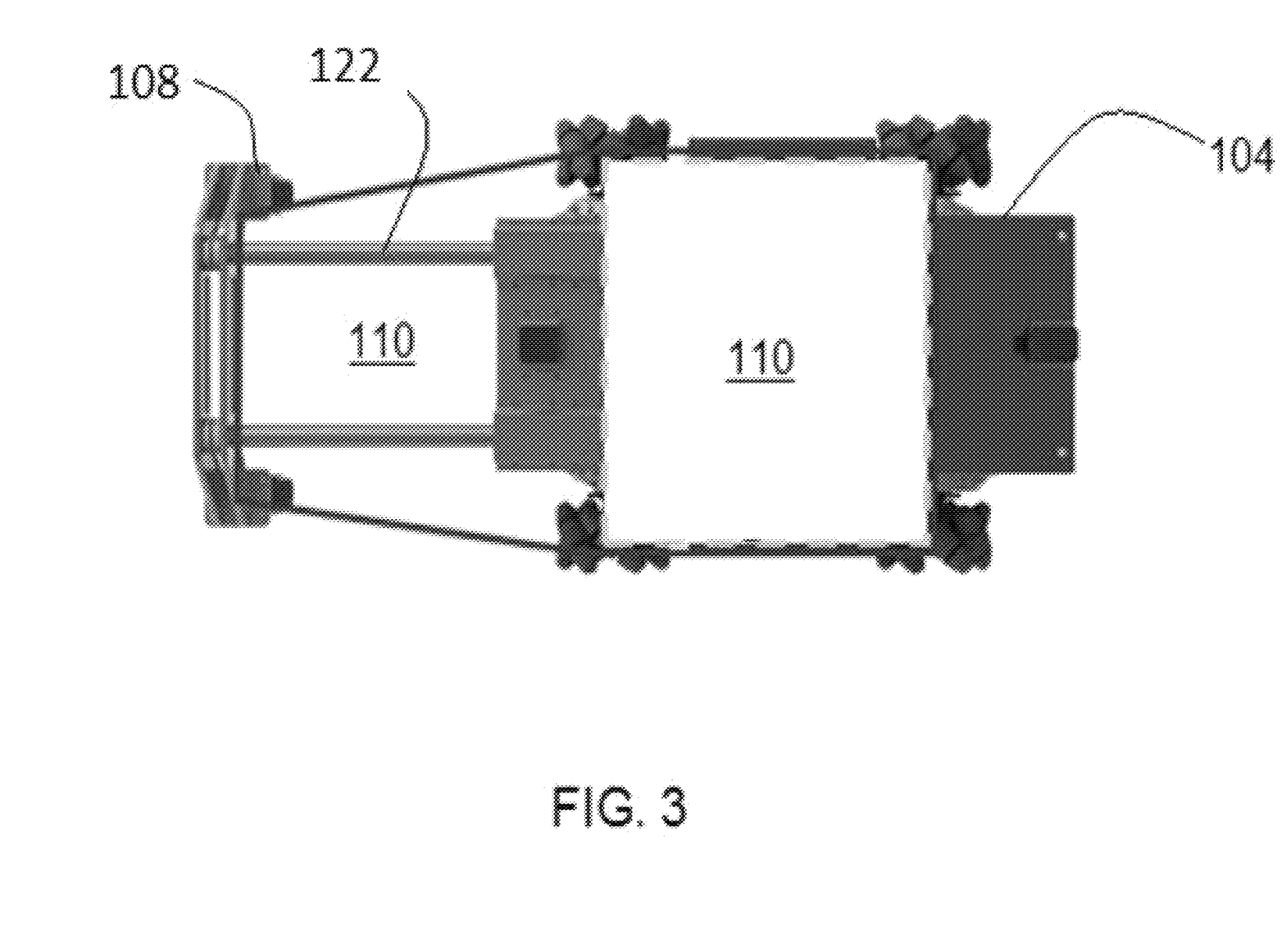
FIG. 3 illustrates an exemplary ZMP stable region within the area of an extended stable zone, in accordance with an embodiment of the present invention.

FIG. 3 illustrates an exemplary ZMP stable region 110 within the area of an extended extender portion, in accordance with an embodiment of the present invention. In some embodiments, the ZMP stable region 110 may include an area in proximity to the extreme ends of at least one support leg. Those skilled in the art, in light of the present teachings will recognize that a robot that stays within the ZMP stable region may provide stability in legged robot locomotion for achieving body dynamic stability while walking In some embodiments, the ZMP stable region may include a polygon area within the robot foothold. In some embodiments, if at least one legged support extends beyond the ZMP stable region, the robot may destabilize, even if the center of gravity satisfies the stability condition. Those skilled in the art, in light of the present teachings will recognize that for a wheeled platform, the zero moment point principals may be applied to determine if the mobile robot stability system is stable when weight lifting is involved.

Figure 4:
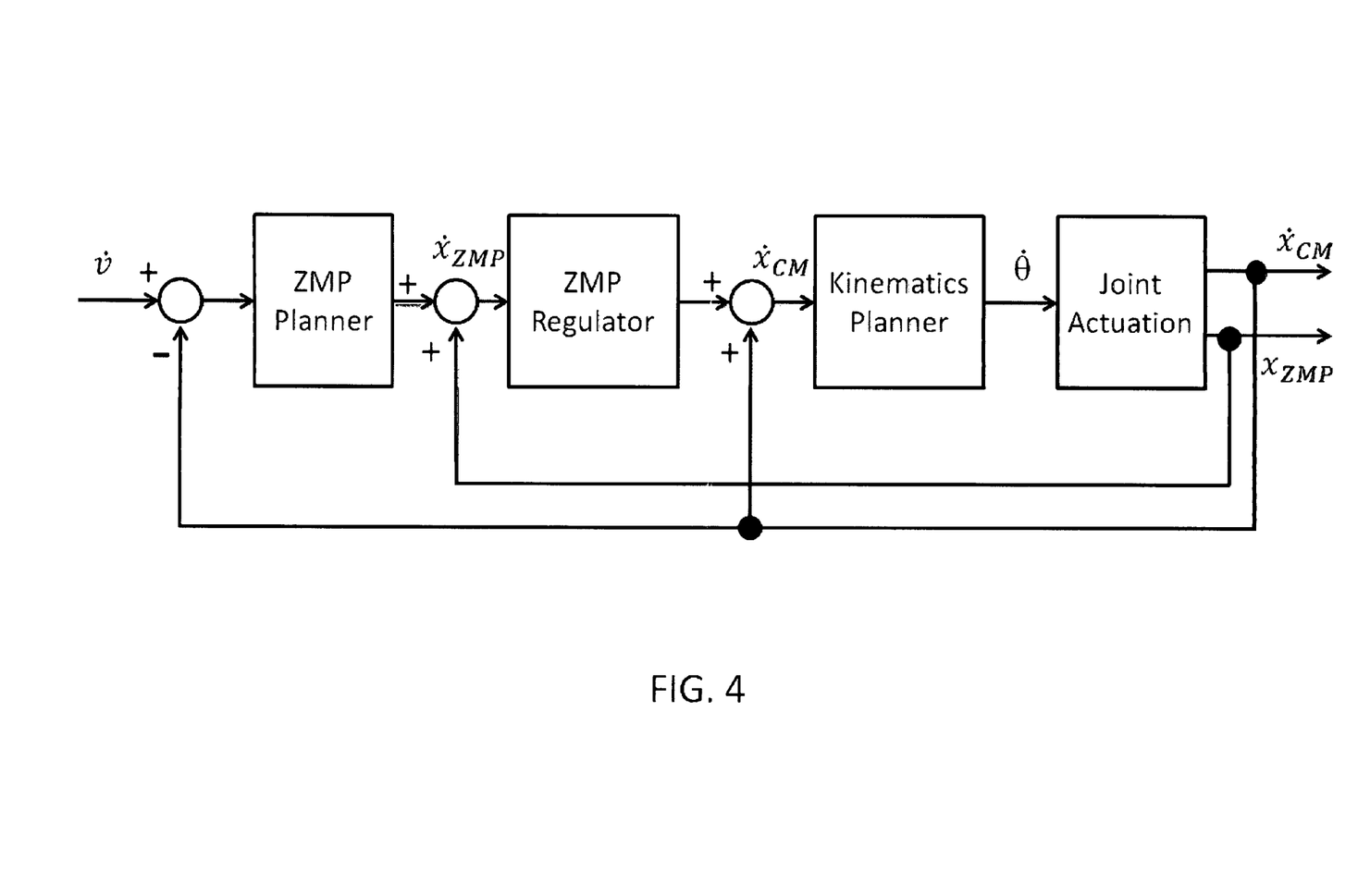
FIG. 4 illustrates an exemplary block diagram of the implementation of a ZMP control mechanism, in accordance with an embodiment of the present invention.
Figure 5A:
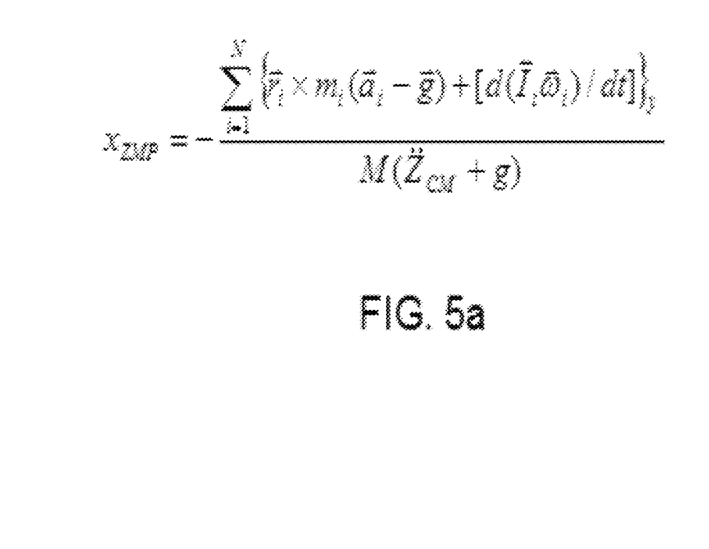
FIGS. 5a, 5b, 5c, and 5d illustrate four exemplary ZMP formulas for calculating the point on the ground surface about which the horizontal component of the moment of ground reaction force is zero, in accordance with an embodiment of the present invention.
Figure 5B:
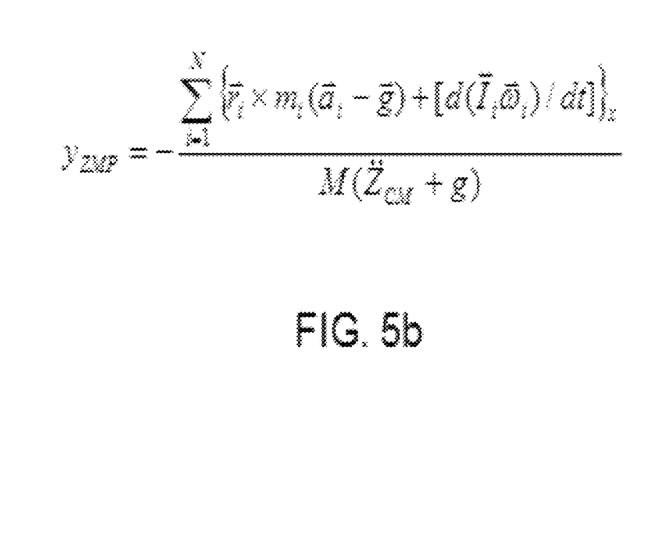
Figure 5C:
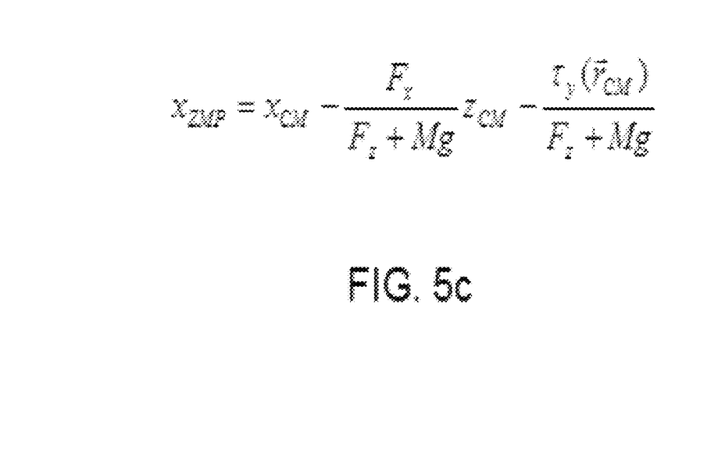
Figure 5D:
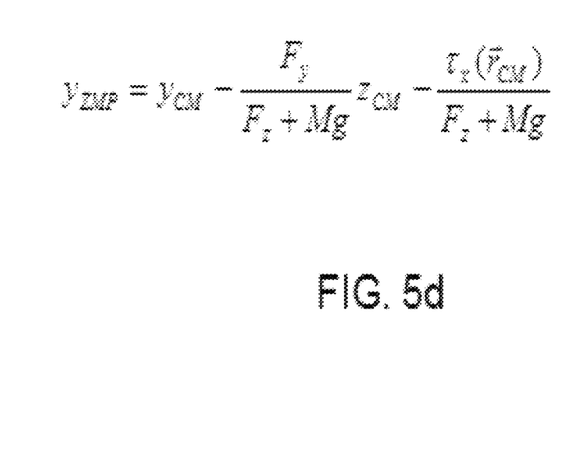

FIG. 4 illustrates an exemplary block diagram of the implementation of a ZMP control mechanism, in accordance with an embodiment of the present invention. In some embodiments, the direct ZMP control mechanism may apply zero moment point principles in many aspects of the robot motion control directly in planning, regulation and robot joint actuation control in an integrative effort. Those skilled in the art, in light of the present teachings will recognize that the planning steps for zero moment point and kinematics precede the actual movements.

FIGS. 5a, 5b, 5c, and 5d illustrate exemplary zero moment point equations for determining the point on the ground surface about which the horizontal component of the moment of ground reaction force is zero, in accordance with an embodiment of the present invention. In some embodiments, two approaches may be utilized in implementing ZMP control to ensure robot operation stability: 1) ZMP margin control, and 2) ZMP regulation. In some embodiments ZMP margin control may be implemented through a traditional robot manipulation process including, without limitation, kinematics control, human-robot interactive control, and the like. The ZMP stability may be assessed in real-time by referencing the ZMP stable region to discern whether the mobile robot stability system is within the specified stability zone. FIGS. 5a, 5b, 5c, and 5d may be efficacious in determining the area of the mobile robot stability system. In some embodiments for computation, the zone moment point ZMP, $\vec{r}_{ZMP}$, may be considered as the point on the ground surface about which the horizontal component of the moment of ground reaction force is zero. In some embodiments, the zero moment point coordinates $x_{ZMP}$ and $y_{ZMP}$ are expressed in FIGS. 5a and 5b. In yet another embodiment, $\vec{r}_{CM}$ may represent the CM, where M is the total body mass, $\vec{r}_i$ is the CM of the i-th link, $m_i$ is the mass of the i-th link, $\vec{a}_i$ is the linear acceleration of the i-th link CM, $\ddot{I}_i$ is the inertia tensor of the i-th link about the link's CM, and $\vec{\omega}_i$ is the angular velocity of the i-th link. Those skilled in the art, in light of the present teachings, will recognize that, given full body kinematics and the mass distribution of a robotic system, FIGS. 5a and 5b may be used to reconstruct a ZMP trajectory. In some embodiments, the ZMP may be expressed as a function of the CM position, net CM force ($\vec{F}=M\vec{a}_{CM}$) and net moment about the CM.

Figure 6A:
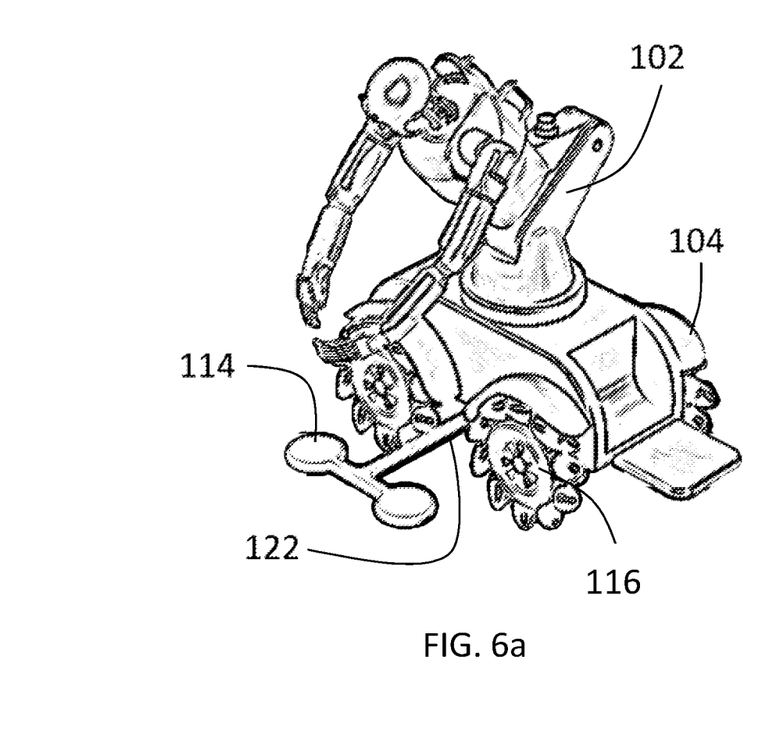
Figure 6B:
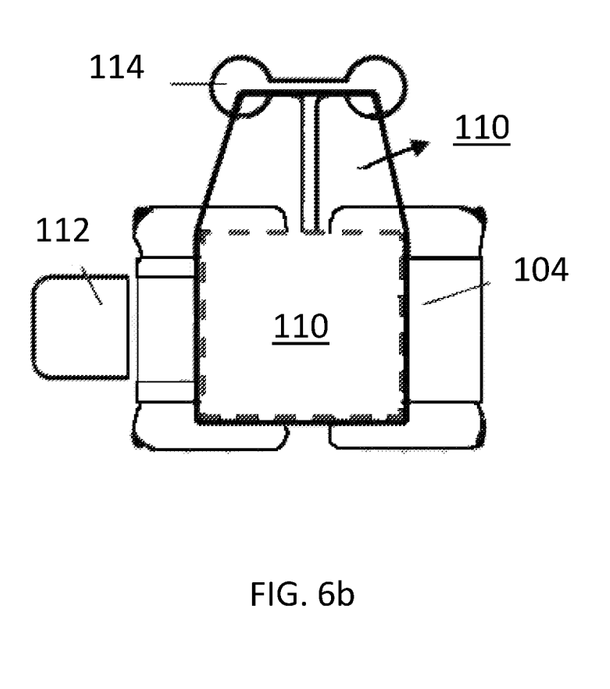

FIGS. 6a and 6b illustrate a detailed perspective view of an exemplary mobile robot stability system with an extended stability zone 110 on the side, in accordance with an embodiment of the present invention, where FIG. 6a shows a robot 102 maneuvering to the side in a small area, and FIG. 6b shows the platform with a ZMP stable region on the side, corresponding to the extension of the side extension portion, in accordance with at least some embodiments of the present invention. In some embodiments, at least one side extension portion may extend to the side of the mobile robot stability system for creating the ZMP stable region during manipulation such as patient lifting and rescuing wounded soldiers in battlefield.

Those skilled in the art will readily recognize, in light of and in accordance with the teachings of the present invention, that any of the foregoing steps may be suitably replaced, reordered, removed and additional steps may be inserted depending upon the needs of the particular application. Moreover, the prescribed method steps of the foregoing embodiments may be implemented using any physical and/or hardware system that those skilled in the art will readily know is suitable in light of the foregoing teachings. For any method steps described in the present application that can be carried out on a computing machine, a typical computer system can, when appropriately configured or designed, serve as a computer system in which those aspects of the invention may be embodied.

Figure 7:
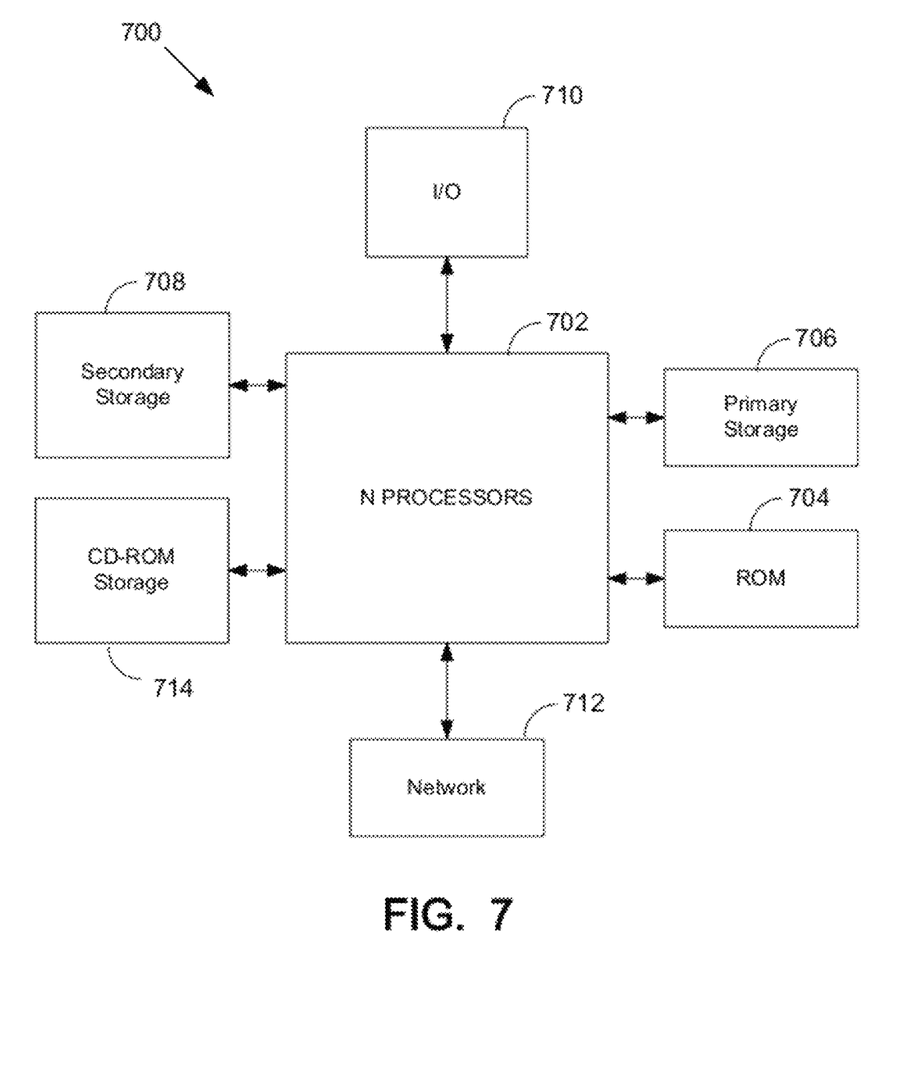
FIG. 7 illustrates a typical computer system that, when appropriately configured or designed, can serve as a computer system in which the invention may be embodied.

FIG. 7 illustrates a typical computer system that, when appropriately configured or designed, can serve as a computer system in which the invention may be embodied. The computer system 700 includes any number of processors 702 (also referred to as central processing units, or CPUs) that are coupled to storage devices including primary storage 706 (typically a random access memory, or RAM), primary storage 704 (typically a read only memory, or ROM). CPU 702 may be of various types including microcontrollers (e.g., with embedded RAM/ROM) and microprocessors such as programmable devices (e.g., RISC or SISC based, or CPLDs and FPGAs) and unprogrammable devices such as gate array ASICs or general purpose microprocessors. As is well known in the art, primary storage 704 acts to transfer data and instructions uni-directionally to the CPU and primary storage 706 is used typically to transfer data and instructions in a bi-directional manner. Both of these primary storage devices may include any suitable computer-readable media such as those described above. A mass storage device 708 may also be coupled bi-directionally to CPU 702 and provides additional data storage capacity and may include any of the computer-readable media described above. Mass storage device 708 may be used to store programs, data and the like and is typically a secondary storage medium such as a hard disk. It will be appreciated that the information retained within the mass storage device 708, may, in appropriate cases, be incorporated in standard fashion as part of primary storage 706 as virtual memory. A specific mass storage device such as a CD-ROM 714 may also pass data uni-directionally to the CPU.

CPU 702 may also be coupled to an interface 710 that connects to one or more input/output devices such as such as video monitors, track balls, mice, keyboards, microphones, touch-sensitive displays, transducer card readers, magnetic or paper tape readers, tablets, styluses, voice or handwriting recognizers, or other well-known input devices such as, of course, other computers. Finally, CPU 702 optionally may be coupled to an external device such as a database or a computer or telecommunications or internet network using an external connection as shown generally at 712, which may be implemented as a hardwired or wireless communications link using suitable conventional technologies. With such a connection, it is contemplated that the CPU might receive information from the network, or might output information to the network in the course of performing the method steps described in the teachings of the present invention.

All the features or embodiment components disclosed in this specification, including any accompanying abstract and drawings, unless expressly stated otherwise, may be replaced by alternative features or components serving the same, equivalent or similar purpose as known by those skilled in the art to achieve the same, equivalent, suitable, or similar results by such alternative feature(s) or component(s) providing a similar function by virtue of their having known suitable properties for the intended purpose. Thus, unless expressly stated otherwise, each feature disclosed is one example only of a generic series of equivalent, or suitable, or similar features known or knowable to those skilled in the art without requiring undue experimentation.

Having fully described at least one embodiment of the present invention, other equivalent or alternative methods of implementing ZMP stability principals during heavy lifting or rigorous maneuvering according to the present invention will be apparent to those skilled in the art. Various aspects of the invention have been described above by way of illustration, and the specific embodiments disclosed are not intended to limit the invention to the particular forms disclosed. The particular implementation of the mobile robot stability system may vary depending upon the particular context or application. By way of example, and not limitation, the mobile robot stability system described in the foregoing were principally directed to enhance the stability of the mobile robot stability system, especially while lifting heavy weights; however, similar techniques may instead be applied to a unicycle robot that must traverse tight areas, and also balance numerous objects which implementations of the present invention are contemplated as within the scope of the present invention. The invention is thus to cover all modifications, equivalents, and alternatives falling within the spirit and scope of the following claims. It is to be further understood that not all of the disclosed embodiments in the foregoing specification will necessarily satisfy or achieve each of the objects, advantages, or improvements described in the foregoing specification.

Claim elements and steps herein may have been numbered and/or lettered solely as an aid in readability and understanding. Any such numbering and lettering in itself is not intended to and should not be taken to indicate the ordering of elements and/or steps in the claims.

What is claimed is:

1. A system comprising:
a platform, wherein said platform is configured for locomotion in a plurality of directions over a surface, said platform comprising a mounting portion, wherein said mounting portion is operable to generally couple with a robotic unit;
a robotic unit, wherein said robotic unit is configured for dexterous manipulation comprising lifting of at least one object, in which said robotic unit is coupled with said mounting portion;
an extender portion, said extender portion comprising at least one extender unit, wherein said at least one extender unit being coupled with said platform and being configured for controlled extension beyond said platform to generally stabilize said system at least during said manipulation by said robotic unit, said at least one extender unit comprising at least two parallel supporting bars;
said at least one extender unit further comprising at least two wheeled supporters, said two wheeled supporters being coupled to said two parallel supporting bars, said at least two parallel supporting bars being configured to slidably extend and retract said extender unit substantially horizontally to maintain dynamic stability during said dexterous manipulation, in which said two wheeled supporters are configured to carry said robotic unit in a variety of directions;
wherein said at least one extender unit is configured to slidably extend or retract said at least two parallel supporting bars operable to prevent said robotic unit from tipping over, and wherein a controlled extension of said parallel supporting bars during said lifting of at least one object expands a zero moment point stable region;
a motor actuator, wherein said motor actuator is configured to generally provide power to activate said at least one extender unit; and
a control unit, said control unit comprising at least one zero moment point controlling unit being configured to be operable for at least determining a center of gravity and a zero moment point for the system and for at least controlling an extension of said extender unit.

2. The system as recited in claim 1, said platform further comprising an approximately square or rectangular shaped platform, wherein said zero moment point stable region for the system with said controlled extension of said extender unit comprises a generally polygonal area within an area defined by said platform and said at least one extender unit, in which said polygonal area is an extended zero moment point stable region, and wherein said robotic unit is configured to move with dynamic stability by at least retaining its center of gravity within said extended zero moment point stable region.

3. The system as recited in claim 2, in which said controlling unit is further operable for dynamically determining zero moment points during at least said manipulation, in which said controlling unit further comprises a posture control configured to dynamically control a body posture of said robotic unit and enhance stability of said system.

4. The system as recited in claim 3, in which said controlling unit is further operable for dynamically estimating said stability of the system, from said zero moment points, during at least said manipulation, wherein said system further comprises a side extension portion, and in which said side extension portion is configured to extend to a side portion of said platform to create an additional zero moment point stable region to a proximate side of said platform during which said robotic unit is lifting at least one object.

5. The system as recited in claim 4, in which said controlling unit is further operable to control said body posture of said robotic unit during at least said manipulation to maintain said zero moment points within said zero moment point stable region.

6. The system as recited in claim 1, in which said controlling unit is further operable for controlling a posture of said robotic unit during said locomotion of said platform to maintain said zero moment points within a zero moment point stable region of said platform.

7. The system as recited in claim 1, in which said controlling unit is further operable for planning for said zero moment points and dynamics.

8. The system as recited in claim 1, in which said extender unit is further configured to extend beyond an end portion of said platform.

9. The system as recited in claim 1, in which said extender unit is further configured to extend beyond a side portion of said platform.

10. The system as recited in claim 1, said extender unit further comprises at least one wheel operable for contacting the surface.

11. A system comprising:
a platform, said platform being configured for locomotion in a plurality of directions over a surface, said platform comprising a mounting portion, said mounting portion being operable to generally couple with a robotic unit;
a robotic unit being configured for dexterous manipulation comprising lifting of at least one object, wherein said robotic unit is coupled with said mounting portion;
an extender portion, wherein said extender portion comprises at least one extender unit that is configured to engage with said platform and further configured for controlled extension beyond said platform to contact the surface to stabilize the system at least during said manipulation by said robotic unit, in which said at least one extender unit comprises at least two parallel supporting bars being that are configured to slidably extend and retract horizontally;
said at least one extender unit further comprising at least two wheeled supporters, wherein said two wheeled supporters are configured to join to said at least two parallel supporting bars, and wherein said at least two parallel supporting bars are configured to slidably extend and retract said extender unit horizontally;
wherein said at least one extender unit is configured to slidably extend or retract said at least two parallel supporting bars operable to prevent said robotic from tipping over, and wherein a controlled extension of said at least two parallel supporting bars during said lifting of at least one object expands a zero moment point stable region; and
a controlling unit that is configured to be operable for determining a proximate center of gravity and a zero moment point for the system, for controlling an extension of said extender unit, for determining said zero moment point stable region for the system, for dynamically determining proximate zero moment points during at least said manipulation and said locomotion of said platform, for dynamically estimating a stability of the system, from a zero moment points methodology, during at least said manipulation and said locomotion of said platform, for controlling a posture of said robotic unit during at least said manipulation and said locomotion of said platform to maintain said zero moment points within said zero moment point stable region, and for planning for said zero moment points and dynamics.

12. The system as recited in claim 11, said platform further comprises an approximately square or rectangular shaped platform, wherein said extender unit is configured to generally extend beyond an end portion of said platform.

13. The system as recited in claim 11, in which said extender unit further comprises at least a side extension portion, and in which said side extension portion is configured to substantially extend to a side portion of said platform to create an additional zero moment point stable region to a proximate side of said platform during which said robotic unit is lifting at least one object.

14. The system as recited in claim 11, in which said extender unit further comprises at least one wheel for contacting the surface, and in which said controlling unit further comprises a posture control configured to dynamically control a body posture of said robotic unit and enhance said stability of said system.

\* \* \* \* \*